(12) United States Patent
Gart et al.

(10) Patent No.: US 6,187,030 B1
(45) Date of Patent: Feb. 13, 2001

(54) PHOTODYNAMIC THERAPY METHOD

(75) Inventors: Mark B. Gart, Newport Beach, CA (US); Claudio Cesati, Como (IT)

(73) Assignee: MBG Technologies, Inc., Newport Beach, CA (US)

( * ) Notice: Under 35 U.S.C. 154(b), the term of this patent shall be extended for 0 days.

(21) Appl. No.: 09/166,398

(22) Filed: Oct. 5, 1998

Related U.S. Application Data

(62) Division of application No. 08/697,957, filed on Sep. 4, 1996, now Pat. No. 5,849,027.

(51) Int. Cl.$^7$ .................................................. A61N 5/00
(52) U.S. Cl. ................................................ 607/93; 607/88
(58) Field of Search ............................ 607/88–93; 606/2, 606/3, 10, 13–17

(56) References Cited

U.S. PATENT DOCUMENTS

| | | | |
|---|---|---|---|
| 4,782,818 | * 11/1988 | Mori | 607/88 |
| 4,930,504 | * 6/1990 | Diamantopoulos et al. | 607/88 |
| 5,101,452 | 3/1992 | Krebser et al. | 362/19 |
| 5,405,368 | * 4/1995 | Eckhouse | 607/88 |
| 5,441,531 | * 8/1995 | Zarate et al. | 607/88 |
| 5,755,752 | * 5/1998 | Segal | 607/89 |
| 5,843,143 | * 12/1998 | Whitehurst | 607/88 |
| 5,849,027 | * 12/1998 | Gart et al. | 607/93 |

FOREIGN PATENT DOCUMENTS

| | | |
|---|---|---|
| 2272278 | 5/1994 | (GB) . |
| WO 89/00871 | * 2/1989 | (WO) . |

* cited by examiner

*Primary Examiner*—Linda C. M. Dvorak
*Assistant Examiner*—Bryan K. Yarnell
(74) *Attorney, Agent, or Firm*—George W. Wasson

(57) ABSTRACT

A method for photodynamic treatment of diseases using a source of noncoherent light energy with filtering and focusing devices for producing radient energy in a broad bandwidth, the radient energy is transported to an area for disease treatment through a flexible fiber optic light guide. The light guide includes filtering and focusing devices in the light guide for selecting radient energy of a particular wavelength in order to photoactivate a specific theraputic disease treatment.

7 Claims, 2 Drawing Sheets

PHOTODYNAMIC THERAPY METHOD

This application is a Divisional application from Ser. No. 08/697,957, filed Sep. 4, 1996 now U.S. Pat. No. 5,849,027 by the present inventor for PHOTODYNAMIC THERAPY METHOD AND APPARATUS.

This invention relates to a method and apparatus for delivering photodynamic therapy treatments to body parts and surfaces. More particularly, the invention relates to methods and apparatus for producing and delivering optical light energy in controlled frequency and intensity for theraputic treatment of various dermatological and internal diseases in a convenient manner and with a convenient delivery apparatus.

FIELD OF THE INVENTION

The medical community has long investigated the increased healing effects of the sun on dermatological diseases. The advent of modern medicine continues this investigation and numerous research facilities are now documenting these healing effects. As most medical conditions require a unique light source the rush to implement these procedures has been impeded. It is also known that theraputic creams and ointments have enhanced effects when combined with light activation, but each disease and its photo theraputic cream or ointment may require a specific light source. The dedication of a light source to a specific treatment could require the unnecessary duplication of equipment and consume large areas of space just for accommodating the equipment. Physicians, hospitals and clinics might have the required space but presently lack the required funding for the duplicative required equipment. One solution to this problem is the use of one base unit with electromagnetic spectrum adapters which control, regulate and administer the correct exposure as directed by the attending physician.

It has become known that some medications are more effective or only operative when activated by certain controlled light energy applications. Numerous drug companies are experimenting with the possibilities of medicines which can be activated by external light sources. Also, several Universities are researching the healing effects of various light frequencies on human tissue. All these programs require different frequencies within the electromagnetic spectrum. It is apparent that there is a need for one device which can operate at many frequencies with suitable controls that will allow doctors, clinic and home treatment with theraputic light for the diseases and the types of medicants that can produce the desired treatments when properly combined.

Many medical suggestions have been made for using laser light to treat or control diseases; however, laser light sources are expensive to construct and control and the delivery of the benefits of laser light can become lost if the cost of delivery becomes prohibitive. The use of controlled noncoherent light for medical treatments at much less expense than laser light has introduced the need for a useful and reasonably inexpensive means for controlling and delivering light energy to an area where medical treatment is to be effected.

Theraputic lamp equipment is shown in U.S. Pat. No. 5,010,452, Krebser et al where an apparatus is disclosed for delivering polarized light for biostimulation. U.S. Pat. No. 5,441,531, Zarate et al discloses an apparatus for delivering photodynamic therapy light to a patient. United Kingdom application 2 272 278 of Colin Whitehurst discloses an incoherent or non-laser light source employing a high intensity lamp, filters and focusing means arranged to yield a light beam having a desired output intensity over a desired area and in a desired bandwidth. Each of these patents illustrates the need for generating preferred light energy in selected frequencies or bandwidths for the medical treatment of a patient.

Missing from these disclosures is an economical and convenient apparatus for controlling the intensity, power and frequencies of the light energy to be delivered and an economical and convenient apparatus for safely delivering and further controlling the light energy in directing and applying the light energy to the desired area on a patient to be treated.

SUMMARY OF THE INVENTION

The present invention includes a photo therapeutic light device in which numerous electromagnetic radiated frequencies can be generated, transported, filtered, focused and power output controlled using the apparatus disclosed. Photodynamic theraputic treatment light energies range from near ultraviolet (about 400 nanometers) to extreme infrared (about 800 nanometers) and, as contemplated here, the range of light energies is about 300 nanometers to about 800 nanometers. The present invention includes a light source with power supply, cooling system, light filament bulb or other suitable source, lenses and filters and a transport mechanism which incorporates fiber optic materials for filtration, focusing light source sizing, and control for intensity of emitted light energies through a mechanically flexible system for delivery of the theraputic light.

An object of the present invention is a convenient combination of a light generating source including filtering, focusing, and power control elements for producing a desired light energy and the addition of a convenient means for transporting, filtering, focusing and power controlling the light energy to deliver the energy to an area to be treated.

Another object of the present invention in accord with the preceding object is the provision of an economical means for developing and delivering photodynamic therapy light energy for theraputic treatment of diseases.

Another object in accord with the preceding object is the use of a fiber optic light transporting device for the delivery of the light energy to the area to be treated.

Another object in accord with the preceding objects is the use of a flexible fiber optic light transporting device in delivering the light energy.

Another object in accord with the preceding objects is a means for coordinating the generating source and the transporting device for particular and designated light energy bandwidths or frequencies to prevent inadvertent connection and delivery of improper theraputic light.

Further objects and features of the present invention will be readily apparent to those skilled in the art from the appended drawings and specification illustrating a preferred embodiment wherein:

DETAILED DESCRIPTION OF THE DRAWINGS

Figure 1:
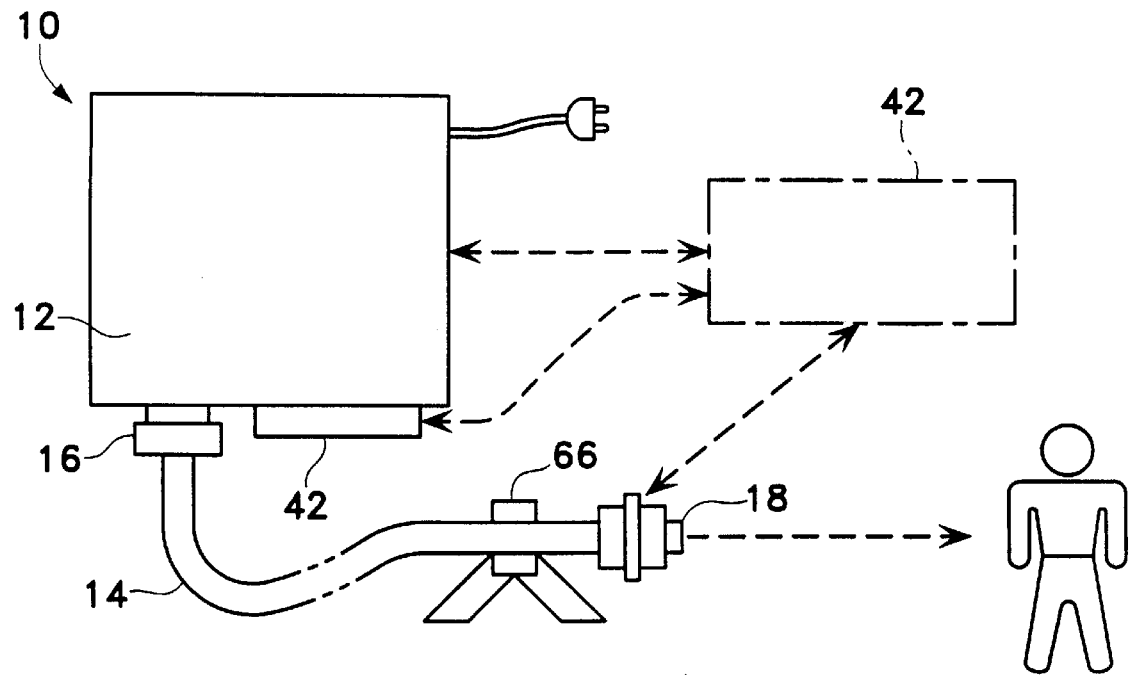
FIG. 1 is an assembly drawing showing the light generating source and the transporting means.

The present invention is an assembly 10 as illustrated in FIG. 1 including a light generating source 12 and a transporting means 14. The source 12 and transporting means are attached to each other at connector 16. The transporting means is flexible and terminates in an exit end at 18 where photo theraputic light energy is radiated. The light generating source 12 will contain the electronic or mechanical systems and components required to provide regulated power for the source, electronic controls and circuitry for controlling the source, light source monitoring and feedback safety circuitry for control of the generated light energy and mechanical interconnect elements for passing the light energies to the transporting means 14.

Figure 2:
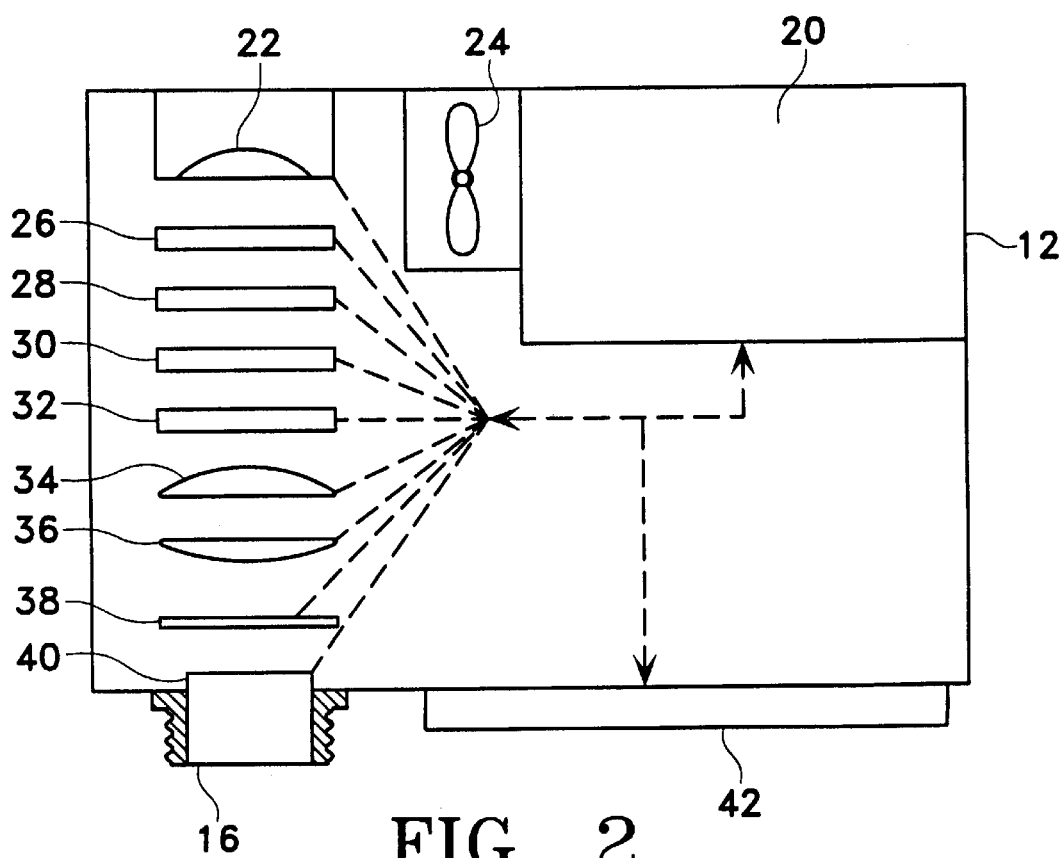
FIG. 2 is a representation of the elements within the generating source of FIG. 1.

FIG. 2 is a representation, partially schematic, of the elements that are included within the light generating source 12; those elements including focusing, filtering and power regulating means for the light energy generated within the source with sensing and feedback means for control of the elements. The source includes a power supply 20 and a means for generating noncoherent light energy 22 powered by the supply. The means for generating noncoherent light energy may be a vacuum rare gas filament bulb or bulb of other conventional design and may include multiple bulbs if greater power is needed. The multiple bulb light source can have the several bulbs arranged in a arc around a reflector that will direct the accumulated light to the filtering and focusing means or other suitable means for focusing the light onto a lens which would collimate the light into one beam. The bulb should be large enough to generate output power in the range of 300 to 400 watts, or higher if needed. A suitable cooling fan and heat extractor 24 is provided to remove excess heat. The bulb should be capable of generating radient energy in the visible and near visible range and be capable of delivering the photodynamic radient energy in desired wavelengths for theraputic treatment purposes. The power generated by the bulb as measured in watts is determined by the medical requirements and can be increased or decreased as required to meet the medical needs.

Between the bulb 22 and the connector 16 there are a group of elements that are used to shutter, filter, focus and power control the generated light energy. An outer shutter dump 26 having a function of controlling the aperture through which the light energy will pass is designed for controlling the beam size of the generated light energy. At this point heat may have to be extracted from the beam and the dump portion of this element accomplishes that purpose. An infrared filter 28 is adapted to extract the light energy in the infrared range to permit the generated and transported light energy to be in the visible and near visible range without the heat rays of infrared. A broad range band pass filter 30 then permits the transmission of the desired photo theraputic energy light rays in the range of 300 nm to 800 nm wavelength. A second band pass filter 32 is provided for fine filtering the transmitted light into specialty frequency ranges for particular theraputic treatments. The filtered transmitted light is then focused first in a gross focusing lens 34 and then, optionally, in a final focusing lens 36. The filtered and focused transmitted light is then passed through a conditioning and density control filter 38 for preparing the transmitted light for exit from the source 12. The conditioned and density controlled transmitted light is then passed to an interconnection system 40 for interconnecting the light to a fiber optic interface at the connector 16. The connector 16 includes a suitable heat sink to withdraw heat from the transmitted light to prevent damage to the fiber optic system, patient or practitioner from excessive heat.

The source 12 includes a control panel 42 with the usual and conventional controls that would be used to control the power to the bulb and the monitoring of the filtering, focusing and power control of the generated and transmitted light energy. The monitoring devices for connection to the control panel are shown in dotted lines; the controls are conventional elements well known in the control arts for sensing the frequency, intensity and spot size of the focused, filtered and power controlled light energy. The controls can be for preliminary or gross adjustments of the light beam with final adjustments made in the transporting means 14 as will be further described hereinafter.

Figure 3:
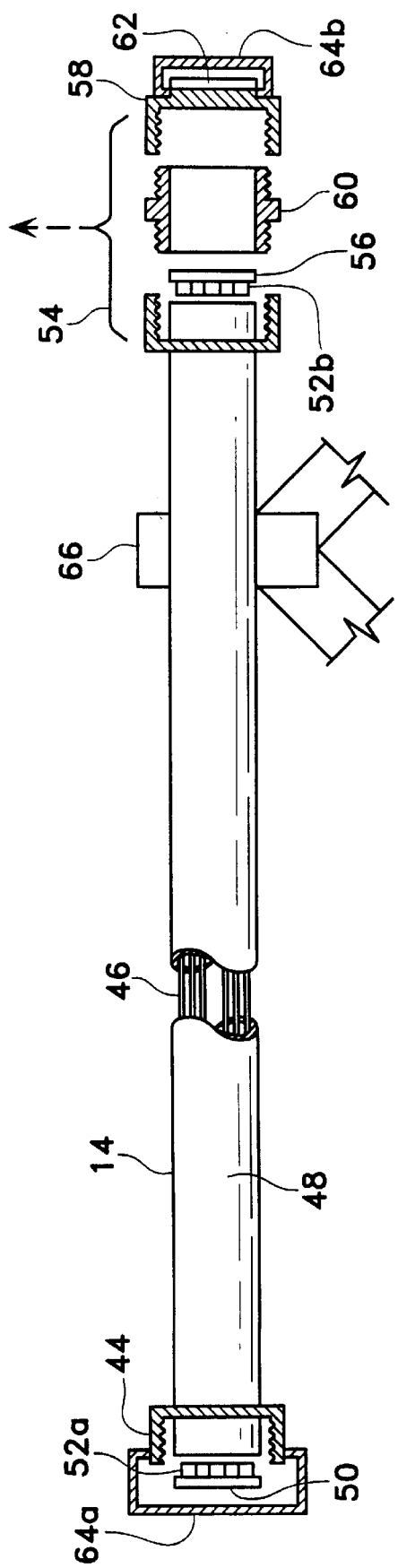
FIG. 3 is a plan view partially in section of the transporting means of FIG. 1.

The generated, filtered and focused light energy available at the connector 16 is then to be used for the theraputic treatment of diseases either external or internal on a patient, but that light energy has to be delivered in some convenient manner to the area to be treated. For that purpose, the electromagnetic energy transporting means or light guide 14 of FIG. 3 is provided with this invention. The transporting means 14 is provided with a connector 44 adapted to be mated with the connector 16 on the light generating source 12. As will be further described later, the connector 44 is preferably constructed and coded to be used for selected light energy transmission and is adapted to be used only with a selected light energy or power to avoid incorrect or improper uses. The transporting means 14 is preferably constructed of fiber optic elements 46 assembled in a bundle within the transporting means and the entire bundle is encased within a shielding exterior cover 48 in a manner to be completely flexible. It should be understood that the transporting means 14 and its interior bundle of optical fibers can be of a wide variety of outer diameter sizes so as to be adapted to be used internally or externally in theraputic treatment programs. The total fiber bundle can range from 0.1 mm to larger than 1.0 cm if the treatment mandates such requirements in deliverable energies or larger spot sizes. Each fiber within the bundle can range from about 0.001 mm to 1.0 mm or larger.

At the input end of the transporting means 14 the connector 44 is provided with a narrow band pass filter 50 which may be selected for a number of separate desired applications; the band pass of this filter will be related to the desired theraputic treatment to be provided. Inside of the filter 50 and between the filter and the fiber bundle a fiber bundle and filter interface 52a is provided to couple the light energy from the generating element 12 to the transporting means 14.

At the exit end 18 of the transporting means 14 the fiber bundle terminates in another fiber bundle and filter interface 52b for coupling the fiber bundle to a final focusing and filter assembly 54 to finish the adjustment of the optical energy if that becomes necessary. The filter assembly includes a final narrow band pass filter 56 which may be optional and used to adjust the output energy in about +/−25 mn, a focusing iris 58 for final beam size, a conditioning filter and focusing lens adapter 60. The adapter 60 terminates in an output lens or window 62. These elements at the exit end of the transporting means are provided to permit the user to produce the final adjustment of the spot size, intensity and frequency of the theraputic light energy transmitted along the fiber bundle.

Both the input end of the fiber bundle and the exit end 18 may be provided with end caps 64a and 64b, respectively, to protect the optical portions of the transmitting means when not in use or when disconnected from the light source 12.

As shown in FIGS. 2 and 3, the input end of the fiber bundle 14 at connector 44 is provided with a threaded female adapter for connection to the male threads at the output connector 16 of the light source. These two elements can be provided with additional adapters that will be fitted to the fiber bundle or the generator for selected light frequencies or power and can be color coded, or otherwise distinctly identifiable, for the selected uses. With that adaptation of the connectors, the user of the theraputic apparatus can be visually or sensibly alerted to making the proper connection of fiber bundle and light source.

The fiber bundle 14 can be designed for many different uses both in diameter of the bundle and its length. Limitations on the length and size are mostly economic in that smaller individual optical fibers can be more costly. The total length of the entire fiber bundle and the distance from the light generating source to the patient is one of customer's needs. The fiber bundles can range from several inches (about 10 inches) to several feet (3 feet to 10 feet or more). Smaller diameter bundles will be needed for interior theraputic treatments and larger bundles may be desirable for external treatments.

The fiber bundle may also be provided with a support means 66 as shown in FIGS. 1 and 3. This support means, or others suitably adapted, can support the fiber bundle for holding, aiming and targeting an area that is to be treated while allowing the user of the apparatus to have hands free for other uses.

The drawings show, by dotted lines, a feedback and control connection between the control panel 42 and the filtering, focusing and power control elements of the apparatus. In FIG. 1 the control panel 42 is shown in phantom lines as separated from the light generating source 12 for the purpose of illustrating the placement of the control panel nearer to the user or the patient or the target area or at some other remote area away from the source. It is intended that these feedback and control connections should include monitoring means for spot size, frequencies, intensities, and other conditions such as temperature. The individual elements of the filtering, focusing and power control elements will include appropriate adjustment means, mechanical or electrical, for adjusting the conditions being controlled. The user of the apparatus can also control those elements from the control panel to produce the desired output light energies or the elements within the source 12 can be changed to produce a desired output condition. The control of the filtering and focusing can be done in a broad sense within the light generating source 12 prior to exiting the source at connector 16. The fine tuning and final adjustment of the light beam for spot size, intensity and wavelength can be accomplished, mechanically or electrically, at the filtering and focusing means in the fiber bundle transmission means 14. The final beam exiting from the fiber bundle can be monitored, either internally in the fiber bundle or by a portable meter to measure beam dynamics prior to exposing the patient to the treatment, and the results of the monitoring can be sent to the control panel as represented by the dotted line from the bracket at 54 to the control panel, or the monitoring results can be returned to the control panel through an optical fiber connection. It is also contemplated that a particular setting of filters and focusing means can be "keyed" into the control panel for a particular treatment protocol and those settings could then be accomplished in the light source unit or in the fiber bundle transmission means when it is connected to the light generating source. In that way a single source can be used and a desired theraputic treatment may be more successfully accomplished by transmission tuning. One source can be used to provide a variety of treatments.

It is believed that the present apparatus can be adapted for the treatment of internal and external diseases in humans and other animals. The combination of the controlled photodynamic therapy light energy with selected medications that will be either activated by or enhanced in their effectiveness by the light energy and the ease of directing the light energy to the treatment area makes the present invention economically attractive. It is possible to have a single light energy generating source 12 with broad filtering and focusing adjustments and a plurality of separate transmission means 14 adapted to fine tune the light energy and to direct it to the treatment area. Each of the individual elements such as shutters, filters, focusing means and couplers are intended to be easily changed or replaced as needed to meet additional light energies which future treatments might require. One source can serve several fields of use by adjusting the light source and by attaching the appropriate transmission means. Special connectors can be used to prevent the attachment of an incorrect transmission means to the light source.

Another feature of the transmission means light guide of the present invention is that it can be sterilized easily by the presently know sterilizing processes. In many cases, if an element of a disease treatment apparatus is to be reused by the same or different patients, it is a necessity that the apparatus be sterile or the apparatus cannot be reused. In the case of the present invention, it would be cost prohibitive to consider the transmission means as a disposable item. In that regard, the fiber bundle light guide of the present invention can be sterilized by being autoclaved, irradiated or chemically treated to produce the sterile condition needed for reuse.

Disclosed herein is an apparatus and method for delivering radient energy for theraputically treating diseases in a combination of a source of noncoherent radient light, means for focusing, filtering and power controlling the light to produce a first level of control of the light, a flexible transmission means connected to the light source for transporting the light to a treatment area, means for filtering and focusing the transported light to produce the desired frequency, power and spot size in the radient energy, means for directing the radient energy to a desired treatment area, and a control system for monitoring the focusing, filtering, power level and spot size of the radient energy. The transmission means includes a flexible fiber optic bundle connected to the light source and the connection may be adapted to code individual transmission means to particular treatment protocols with means for preventing incorrect interconnections of the source and transmission means.

The source contemplated herein is a non laser source of electromagnetic energy including radient and light energy generated by a vacuum rare gas or other suitable bulb, for example a halogen bulb, capable of producing energies in about 300 to 800 nanometer wavelength. The source generates a broad band of energies and the transporting means light guide may then narrow that bandwidth to the desired photodynamic energies for theraputic treatment of disease. It should be understood that the fiber optic light guide can include adjustable elements, replaceable elements or could be preset with elements for developing a desired wavelength of energy.

While certain preferred embodiments of the invention have been specifically disclosed, it should be understood that the invention is not limited thereto as many variations will be readily apparent to those skilled in the art and the invention is to be given its broadest possible interpretation within the terms of the following claims.

We claim:

1. A method for producing and delivering photodynamic radient energy for theraputically treating diseases comprising:

a) generating a noncoherent radient light energy, b) focusing, filtering and power controlling said generated radient light energy to produce light energy in a wavelength that will include a desired radient energy for said theraputic treatment of diseases, c) passing said focused, filtered and power controlled light energy to a flexible, fiber optic transporting means, d) in said transporting means further focusing, filtering and treating said transported light energy to produce light energy in substantially the exact light energy wavelength needed to photoactivate a specific theraputic disease treatment, e) and directing said exact light energy to a diseased area to perform said photoactivated photodynamic theraputic treatment of said disease.

2. A method for producing and delivering photodynamic radient energy for theraputically treating diseases comprising:

a) generating a noncoherent radient light energy, b) focusing, filtering and power controlling said generated radient light energy to produce light energy in a wave length that will include a desired radient energy for said theraputic treatment of diseases, c) passing said focused, filtered and power controlled light energy to a flexible, fiber optic transporting means, d) in said transporting means further focusing, filtering and treating said transported light energy to produce light energy in the range of about 10 mw to about 500 mw per square centimeter and a wave length of about 300 to 800 nm and including substantially the exact light energy wave length and power range needed to photoactivate a specific theraputic disease treatment, e) and directing said substantially exact light energy to a diseased area to perform said photodynamic theraputic treatment of said disease.

3. The method of claim 2 wherein said generated noncoherent radient light energy is about 300 to 400 watts and a broad wave length for said focusing, filtering and treating in said transporting means.

4. The method of claim 2 wherein said filtering and focusing of said generated noncoherent radient light energy is to produce light energy in a broad wave length range and a broad power range for said focusing, filtering and treating in said transporting means to photoactivate said theraputic treatment.

5. The method of claim 2 employing a plurality of transporting means each adapted for transporting a different wave length range of light energy in said range of about 300 to about 800 nm wave lengths and each including means for focusing, filtering and treating input radient light energy, the selection of one of said plurality of transporting means, and filtering, focusing and treating said transported radient light energy in said selected transporting means to produce output radient energy for said substantially exact light energy wave length and power range need to photoactivate a specific theraputic disease treatment.

6. The method of claim 2 wherein focusing, filtering and treatment of said transported light energy in said transporting means produces a light energy to a diseased area in a spot size of about 1 to about 100 square centimeters.

7. A method for delivering electromagnetic radient energy for photodynamic theraputic treatment of diseases in accord with predetermined medical protocols including pharmaceuticals which respond to radient energy of a prescribed wave length and of a prescribed power range, using an apparatus including:

A) a source for generating broad wave length noncoherent electromagnetic radient light energy, said source including radient energy filtering and focusing means, said filtering and focusing means comprising means for providing controlled radient energy in a broad wave length range and broad power range at an output connection from said source, B) a plurality of selectable, removable and changeable flexible radient energy transporting means, means for removably connecting said selectable transporting means individually to said radient energy source at said output connection, means within each of said selectable transporting means for controlling output radient energy from said transporting means, said controlling means comprising means in said transporting means for focusing, filtering and power regulation of input radient energy from said source to provide controlled output radient energy from said transporting means, said plurality of selectable transporting means including individual transporting means for supplying output radient energy in the range of prescribed wave length and prescribed power range over a prescribed spot size, the method steps comprising:

a) generating said noncoherent radient light energy in said source, said generated light energy being about 300 to 400 watts and a broad wave length, b) focusing, filtering and power controlling said generated radient light energy in said source to produce light energy in a wave length within said broad wave length range and broad power range that will include a desired radient light energy for said theraputic treatment of diseases, c) selecting from said plurality of flexible radient energy transporting means the transporting means that is identified with a predetermined medical protocol, and connecting said selected transporting means to said source at said output connection, d) passing said focused, filtered and power controlled radient light energy to said selected flexible radient energy transporting means at said output connection, e) in said radient energy transporting means focusing, filtering and treating said transported radient light energy to produce radient light energy in the range of about 10 mw to about 500 mw per square centimeter and a wave length of about 300 to 800 nm and including substantially the exact light energy wave length and power range needed to photoactivate said predetermined medical protocol including pharmaceuticals for a specific theraputic disease treatment, f) and directing said substantially exact radient light energy by said transporting means to a diseased area in a spot size of about 1 to about 100 square centimeters to perform said photodynamic theraputic treatment of said disease.

* * * * *